United States Patent
Pitts et al.

(10) Patent No.: US 8,529,257 B2
(45) Date of Patent: *Sep. 10, 2013

(54) AEROSOLIZED CERAMIC PORCELAINS AND GLAZE COMPOSITION

(75) Inventors: Phillip G. Pitts, Franklin, TN (US); James R. Vinson, Clarksville, TN (US)

(73) Assignee: EnameLite, LLC, Clarksville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/142,983

(22) Filed: Jun. 2, 2005

(65) Prior Publication Data

US 2005/0223942 A1    Oct. 13, 2005

Related U.S. Application Data

(62) Division of application No. 10/622,090, filed on Jul. 17, 2003, now Pat. No. 7,018,465.

(60) Provisional application No. 60/397,664, filed on Jul. 22, 2002.

(51) Int. Cl.
*A61C 5/00* (2006.01)
*A61K 6/06* (2006.01)

(52) U.S. Cl.
USPC ............... 433/100; 433/229; 106/35

(58) Field of Classification Search
USPC .......... 106/35, 415, 404, 418, 425, 430, 106/434, 435, 450, 431, 436, 438, 439, 440, 106/441, 442, 453, 454, 456; 428/403; 433/215, 121.1, 206; 501/17, 35, 64
See application file for complete search history.

(56) References Cited

U.S. PATENT DOCUMENTS

| | | | | |
|---|---|---|---|---|
| 4,176,205 A | | 11/1979 | Molina | |
| 4,353,991 A | * | 10/1982 | Van Ness et al. | 501/20 |
| 4,357,287 A | * | 11/1982 | Schonert | 264/39 |
| 4,641,974 A | * | 2/1987 | Church | 366/342 |
| 5,009,709 A | * | 4/1991 | Ibsen et al. | 106/35 |
| 5,173,114 A | * | 12/1992 | Heurtaux | 106/35 |
| 5,300,324 A | * | 4/1994 | Croft et al. | 427/376.2 |
| 5,679,144 A | * | 10/1997 | Thiel et al. | 106/35 |
| 5,942,559 A | | 8/1999 | Voser et al. | |
| 6,004,894 A | * | 12/1999 | Faust et al. | 501/17 |
| 6,022,819 A | * | 2/2000 | Panzera et al. | 501/20 |
| 6,059,949 A | | 5/2000 | Gal-Or et al. | |
| 6,299,674 B1 | | 10/2001 | Takamuru et al. | |
| 6,428,614 B1 | * | 8/2002 | Brodkin et al. | 106/35 |
| 6,428,725 B1 | | 8/2002 | Wolz | |
| 6,444,597 B1 | * | 9/2002 | Sato et al. | 501/20 |
| 6,722,271 B1 | * | 4/2004 | Geddes et al. | 101/33 |
| 7,018,465 B2 | * | 3/2006 | Pitts et al. | 106/415 |
| 2001/0002994 A1 | * | 6/2001 | Masuhara et al. | 424/49 |

FOREIGN PATENT DOCUMENTS

| | | |
|---|---|---|
| EP | 364281 | 10/1989 |
| WO | WO 04000154 | 12/2003 |

* cited by examiner

*Primary Examiner* — Pegah Parvini
(74) *Attorney, Agent, or Firm* — Stites & Harbison PLLC; Nicolo Davidson; Richard S. Myers, Jr.

(57) ABSTRACT

A spray glaze or opaque composition for coating dental restorations and other surfaces and objects such as hobby ceramics that comprises about 4 to about 50 weight % glaze material, about 5 to about 60 weight % restoration wetting agent, and about 10 to about 90% non CFC propellant. An opaque composition further comprises about 5 to about 30% opaque material.

10 Claims, No Drawings

AEROSOLIZED CERAMIC PORCELAINS AND GLAZE COMPOSITION

PRIORITY INFORMATION

The present application is a divisional application of, and claims priority of, U.S. application Ser. No. 10/622,090, filed Jul. 17, 2003 now U.S. Pat. No. 7,018,465, which claims priority of U.S. application Ser. No. 60/397,664, filed Jul. 22, 2002, the contents of which are incorporated herein by reference in their entirety.

FIELD OF THE INVENTION

The present invention relates generally to the dental and ceramic pottery fields and more particularly to an aerosol ceramic spray that allows a ceramist to porcelain, opaque, glaze, and/or glass coatings to an item such as a dental ceramic restoration or object of pottery.

The present invention also relates to methods of coating an item such as a dental ceramic restoration, small metal object, or object of pottery. The method of the present invention is easier to perform than prior art methods.

Accordingly, the spray and method of the present invention increases the efficiency of a ceramist while decreasing the amount of time and amount of materials usually required by a ceramist to apply such coatings. The spray of the present invention provides an even coating and consistent quality application.

The present invention also relates to the fingerprinting art by aiding a person in "lifting" fingerprints from a surface.

BACKGROUND OF THE INVENTION

For years, dentists have practiced the art of replacing missing teeth of their patients with various materials, including metal restorations. Typically, the metal restorations comprise precious metals such as gold and silver. In many cases, the natural coloring of these metal restorations were not pleasing to the patient if they were used to replace anterior or front teeth.

In order to achieve benefits such as maximizing the aesthetic appeal and/or improving the life of the restoration, porcelain-to-metal technology was developed and introduced to the dental profession.

In order to maximize the aesthetic appeal to dental patients, one technique coats the metal with opaque tooth color shaded porcelain that closely matched the patient's natural dentition. In this technique, a mixture of powdered opaque porcelain and distilled water is mixed and the opaque porcelain was applied by brush to mask out the color of the alloy. Then a translucent porcelain is applied and shaped to a tooth form and a transparent glaze is applied with a brush or instrument. However, this is both tedious and time consuming.

More specifically, a typical prior art technique utilized to apply opaque or porcelain to a metal restoration is by brush or instrument. In this process, an opaque (or opaque porcelain) is chosen as closely as possible matching the color and shade of the patient's teeth. The opaque is then mixed with water or an opaque liquid to a creamy consistency. The opaque liquid allows complete wetting of the surface of the restoration so that the opaque will properly attach and coat.

The restoration is carefully cleaned and all dirt and oil is removed. The restoration is then dampened with distilled water or opaque liquid to aid in wetting. Next, the brush is dipped into the opaque mixture and a thin coating of opaque is applied to the restoration by gently tapping the brush and restoration. Once completely covered, the restoration is fired to dry and set the opaque. An opaque mixture of thicker consistency is then made and the application and firing procedure repeated to add a second, thicker coating.

Additionally, a formula of a compatible ceramic stains or colors may be brushed on the restoration and allowed to fire. The glaze is then brushed onto the surface of the restoration and fired so that it appears to be wet and with characterization of stains to match the natural dentition. If desired, an additional application may be applied and fired again to achieve the desired results. The restoration is then finished by polishing any exposed metal alloy and readied for cementation or bonding onto the patients tooth.

While it is possible to apply a somewhat even or smooth coating of opaque or glaze with brush techniques, they require a great deal of familiarity or skill. For example, if glaze or opaque is mixed too thinly it may be hard to control, possibly resulting in a patchy glazed surface on the restoration, and therefore requiring another application of glaze. Furthermore, the patchy or inconsistent surface may exhibit poor bonding characteristics.

Also, a mixture too thick could result in opaque being too thick, resulting in a porcelain restoration with no vitality or translucency. Thick glaze fills up the occlusal anatomy or surface details thereby affecting the life-like appearance of the restoration. In applying a thick opaque and glaze it tends to puddle at the margin areas resulting in thick margins that contributes to periodontal disease: Thick glaze fills in details like cervical grooves of anterior teeth and detailed anatomical grooves of posterior teeth of the restoration causing a light discoloration of the restoration. This results in reduction or grinding away of the glaze to avoid a shade or color mismatch. It may also impinge the patients gum tissue, which could result in periodontal gum disease. A thick coating could also result in a poor bond of glaze to porcelain, undesirable white spots discussed above may also present themselves prominently as well. Additionally, a coating that is too thick may lead to bubbling during firing and poor bonding from incomplete wetting of the alloy surface.

In summary, the brush method is very technique sensitive, requiring a skilled ceramist with knowledge of dental anatomy and tissue sensitivities of patients. Additionally, the time that technician must devote to each restoration is costly.

Another method is an airbrush technique, which involved modifying a standard airbrush apparatus. However, this procedure included the tedious steps using multiple airbrush paint jars, test spraying to check spray consistency, and time consuming cleaning steps. Therefore, the airbrush technique is usually practical in a custom laboratory situation, not in a typical production laboratory.

Accordingly, one of ordinary skill in the dental restoration art or ceramic art recognizes the need for a new, easier technique. The present invention addresses this need. The present invention provides an easier method to apply opaque porcelain, stain and/or glaze multiple units in a fraction of the time it would take a skilled technician to do just one unit. The delivery systems of embodiments of the present invention both simplify the opaque and glaze application in a reliable and smooth coating, while also standardizing the process and reducing the cost of producing finished restorations.

SUMMARY OF THE INVENTION

It is accordingly one object of the present invention to provide a spray delivery system, including an aerosolized ceramic spray, opaque and glaze delivery system that will overcome the above-described limitations and disadvantages of prior art. The present invention fills a need for an improved method of opaqueing and glazing substrates, including metal substrates used by dental restoration artists and objects used by ceramists including, but not limited to ceramic tile and pottery.

It is another object of the present invention to provide a spray composition that allows for a uniform layer of opaque porcelain or glaze to a dental restoration or ceramic item. It is another method of the present invention to provide a spray composition to a dental restoration or ceramic item.

Another object of the present invention is to provide a simple and dependable method for spraying ceramic opaque porcelain and/or glaze in a composition that is easy to use, allowing an individual or technician with minimal amount of experience in glazing procedures to apply a substantially homogeneous opaque or glaze layer of glaze without spattering or dripping to allow the consistent application of a substantially uniform layer of glaze to an object, without puddling for example.

Yet another object is to provide a spray opaque porcelain and/or glaze composition premixed to a desired consistency for immediate, convenient use in applying the composition to dental restorations and other forms of ceramics in an aerosol composition.

Another object of the present invention is to provide a method of coating a dental restoration or a ceramic object comprising applying a spray composition of the present invention.

Another object of the present invention is to provide a spray fingerprint composition that can be used in the process of lifting fingerprints on a surface.

Another object of the present invention is a method of obtaining fingerprints using a spray composition of the present invention.

One embodiment of the present invention is a spray glaze composition for coating dental restorations, or other forms of ceramics desirous of glazing. This composition comprises any percentage by weight of the following ranges: about 4 to about 50% glass frit, about 5 to about 60% carrier or wetting agent, and about 10 to about 90% non-CFC propellant. This composition may also comprise any percentage amount from the following ranges: about 8 to about 40% glass frit, about 8 to about 45% carrier or wetting agent, and about 10-80% non-CFC propellant.

Another embodiment of the present invention is a spray opaque composition that may be used for coating and coloring restorations, crowns, other dental appliances, and other objects where such coating and coloring is desired. An example of the composition comprises any percentage amount of the following ranges (by weight %): about 4 to about 50% glass frit, about 5 to about 40% opaque material, about 5 to about 60% wetting agent, and about 10 to about 90% non-CFC propellant. This composition may also comprise any amount of the following ranges: about 8 to about 25% opaque material, about 8 to about 25% wetting agent, about 12 to about less than 1% to about 5% suspending agent and about 25 to about 80% non-CFC propellant.

Another embodiment is a method of applying a glaze to a dental restoration or ceramic material, comprising: providing a spray glaze composition of the present invention; spraying the composition onto the dental restoration or ceramic material; and optionally firing the restoration or ceramic material to set the glaze.

Another embodiment is a method of applying an opaque to a dental restoration, or ceramic material, comprising: providing a spray opaque composition of the present invention; spraying the composition onto the dental restoration or ceramic material; and firing the restoration or ceramic material to set the opaque.

Another embodiment of the present invention is an aerosolized spray fingerprinting formulation, comprising (weight %): about 5 to about 70% fingerprinting powder; about 5 to about 60% wetting agent; and about 10 to about 80% non-CFC propellant.

Another embodiment of the present invention is a method of obtaining fingerprints, comprising: (1) providing an aerosolized spray fingerprint dusting powder of the present invention; (2) identifying a surface that may contain a latent fingerprint; (3) spraying the surface with the fingerprint dusting powder to actualize latent print; and (4) analyzing actualized print.

These and other objects will be apparent from the present disclosure and claims. Additional substance, advantages and other novel features of the invention will be set forth in part in the description that follows and in part will become apparent to those skilled in the art upon inspection of the following or may be learned with practice of the invention or improved development. Further, the above embodiments are examples of the present invention and not intended to be limiting thereof.

DETAILED DESCRIPTION OF THE INVENTION

Prior art ceramic compositions in aerosol applications typically used, as a suspension agent, chlorofluorocarbons, which are now known to be hazardous. Examples include 1,1,1-trichloroethane and Freon TF 22 propellants. Inhalation or swallowing vapors may irritate the respiratory tract and affect the central nervous system. Over exposure symptoms include headache, dizziness, weakness, and nausea. Higher levels of exposure (>5000 ppm) can cause irregular heartbeat, liver, and kidney damage, fall in blood pressure, cardiovascular damage, unconsciousness and even death. 1,1,1-trichloroethane is also thought by some to be a possible carcinogen. Furthermore, CFC materials are the source of a myriad of environmental problems, including adversely affecting the ozone layer. Therefore, their use is not unacceptable in a ceramic composition for aerosol dispersion. Accordingly, one advantage of the present invention is the non-CFC propellant.

As indicated above, embodiments of the present invention include spraying compositions that may be used to coat objects such as dental restorations. When used herein, the terms glaze and spray glaze are understood as having the same meaning, and represent a coating material that may be applied to surfaces. Examples of the surfaces to which the spray glaze of the present invention may be applied include rental restorations, ceramics, tiles, pottery. Examples of the spray glaze compositions of the present invention comprise glass frit, wetting agents, and propellants.

When used herein, opaque, spray opaque, and opaque porcelain are understood as having the same meaning and represent a coating material that may be applied to surfaces such as dental restorations. Examples of the spray opaque compositions of the present invention comprise an opaque material, wetting agents, and propellants.

Glass Frit

The glass frit is available from many different manufacturers worldwide. In embodiments of the present invention, the same glass frit currently used in the dental profession and hobby ceramist practicing the brush technique may be used in the formulation.

The glass frit may be in the form of either a natural or man-made mixture of inorganic chemical substances. The glass frit is produced by rapidly quenching a molten, complex amalgamation of materials. Such glass frit is available from a number of manufacturers under varying designations.

In embodiments, at least about 90% of the frit have a particle size of about 25 microns and under. In another embodiment, at least about 90% of the fit have a particle size of about 20 microns and under. In another embodiment, at least about 75% of the frit have a particle size of about 15 microns and under. In another embodiment, at least about 90% of the frit have a particle size of about 15 microns and under. In another embodiment, at least about 75% of the frit have a particle size of about 10 microns and under. In another embodiment, at least about 90% of the frit have: a particle size of about 10 microns and under. Further, in embodiments of the present invention, at least about 75% of the frit have a particle size of about 8 microns and under. In another embodiment, at least about 90% of the frit have a particle size of about 8 microns and under.

One source of glass frit is the Ferro Corporation, Coating Division, located in Cleveland, Ohio. 3227 leadless frit available from Ferro is an example of glass frit of the present invention. Further, the frit can be milled such as ball milled or jet milled in a ceramic mill to arrive at the preferred particle size.

Because of varying percentages of chemical components in the various glass frit formulations available from manufacturers, the intrinsic characteristics of the glass frit also vary. As a result, the particular weight percentages of the individual components of the glaze composition may need to be adjusted across the range set forth above to provide proper and consistent results.

In examples of the present invention, the glass frit is present in amounts ranging from about 4 to about 50 weight % of the total composition. In other examples, this glass frit is present in an amount of from about 8 to about 35%. In other examples, this range is from about 9 to about 17%.

Opaque Material

The opaque material of the present invention may be in the form of glass frit and natural or man made oxides such as feldspar or a feldspar mixture. Such material is available from a number of different manufacturers under varying designations. The same opaque material currently utilized by technicians practicing the brush or instrument and air brush application technique may be used.

Examples of opaque material of the present invention include Ceramco, Inc. of East Windsor, N.J., Williams Dental Company of Buffalo, N.Y., Dentsply, Inc. of York, Pa. and Vident, Inc. of Baldwin Park, Calif. Examples include Ceramco A-2 shade opaque, Vita A-2, and Williams Dental Company Wob-1 opaque.

Because of varying percentages of, for example, man made and natural feldspar in the various opaque material formulations available from these manufacturers, the intrinsic characteristics of the opaque material also vary. As a result, the particular weight percentages of the individual components of the spray opaque composition may, of course, need to be adjusted across the range as discussed above to provide proper and consistent results. In embodiments of the present invention, the opaque material is present in an amount from about 10-40%. Furthermore, in embodiments of the present invention, the opaque material is present in an amount of from about 15-30%. Additionally, in embodiments of the present invention, the opaque material is present in amounts of from about 12-25% (by weight %) of the total composition.

It is preferred that at least about 70% of the opaque material has a particle size of about 25 microns and under. In another embodiment, at least about 90% of the opaque material has a particle size of about 25 microns and under. In another embodiment, at least about 70% of the opaque material has a particle size of about 20 microns and under. In another embodiment, at least about 90% of the opaque material has a particle size of about 20 microns and under. In another embodiment, at least about 70% of the opaque material has a particle size of about 15 microns and under. In another embodiment, at least about 90% of the opaque material has a particle size of about 15 microns and under. In another embodiment, at least about 70% of the opaque material has a particle size of about 10 microns and under. In another embodiment, at least about 90% of the opaque material has a particle size of about 10 microns and under.

Wetting and Suspension Agents

The wetting and/or suspension agents or carrier best suited for utilization in the glaze composition are those that are used in common everyday use by the medical and dental professions. They do not react with other components of the composition and that are fairly easy to volatize yet do not represent a health, safety, or environment hazard during the spraying or drying of the glaze.

An example of the wetting agent utilized in the present invention is preferably an alcohol. A further example is a 99% anhydrous isopropyl alcohol that is standard in many home cleaners, air fresheners, etc., and medical aerosols used in hospitals and medical facilities. Other preferred alcohols include methyl, ethyl and isopropyl or any mixtures thereof. This wetting agent is effective in maintaining in suspension so as to provide smooth, even, and consistent spraying action without clogging, sticking or splattering.

It should be recognized, however, that alcohols other than anhydrous isopropyl alcohol could be utilized. Purely for exemplary purposes only, the following are examples: methyl alcohol, ethyl alcohol, and any mixture of methyl, ethyl, and isopropyl alcohol. In any event, use of these alcohols in anhydrous form is preferred.

Preferred wetting agents provide very good wetting action and are "water-free." Therefore, there is no freezing of water droplets as the composition cools during spraying. This is a significant feature since freezing water droplets cause the formation of opaque platelets that lead directly to spotting and an inconsistent coating.

The wetting agent of the present invention may also inherently perform the function of a suspension agent. The suspending agent helps provide desired characteristics for the spray opaque composition of the present invention and helps prevent insufficient wetting of the restoration, as well as spray orifice clogging, valve sticking and opaque spattering. Alternatively, a separate suspension agent may be used in the formulations of the present invention.

Typically, the wetting agent is present in an amount ranging anywhere from about 5 to 80%. In other embodiments, the wetting agent is present in an amount ranging anywhere from about 6 to 50%. In other embodiments, the wetting agent is present in an amount ranging anywhere from about 12-50%. In other embodiments, this range is anywhere from about 20-30% (weight %).

Examples of the wetting and suspension agents of the present invention include vinylpyrrolidone/vinyl acetate copolymer and propylene glycole.

Propellant

The propellant used in connection with the present invention is a non-CFC propellant. One propellant that may be used is, a hydrocarbon propellant. Further examples include isobutane, butane or any mixtures thereof. While spray pressures may range between about 17-132 psig, for best results and the most consistent spray characteristics, the compositions of the present invention are packaged at a pressure in the range of between about 17-56 psig.

The butane and isobutane hydrocarbon propellants are available, for example, from Aeropres Corporation, Shreveport, La. under the designation of A-17, A-31 up to the strongest pressure of A-132 propellants. The non-CFC propellant of the present invention may be present in the composition in amounts ranging anywhere from about 10-90%, about 30-90%, and about 40-90% by weight of the total composition.

To achieve the foregoing and other objects and in accordance with the purposes of the present invention as described herein, a spray opaque composition is provided. An example of such composition is a composition that comprises a spray opaque composition that comprises, in weight, about 5% to about 60% opaque material, 4 to about 40% glass frit, about 8 to about 60% wetting and or suspension agent, and about 10 to about 90% non-CFC propellant. Other embodiments have about 75-85% propellant. The spray opaque composition of the present invention may be sprayed on a dental restoration or other material where it is desired to provide a opaque porcelain coating.

Likewise, an example of a spray glaze composition comprises, in weight, about 4 to about 30% glass frit, about 10 to about 80% wetting and or suspension agent, and about 10 to about 90% non-CFC propellant. Other embodiments include about 55-65% propellant. A further example of the spray composition of the present invention is a composition that includes about 14% glass frit, about 27% anhydrous methyl, ethyl and/or isopropyl alcohol, and about 58% propellant (+/− about 5% for each range). These percentages may be adjusted depending on the surface that is to be glazed. The user should desire a sufficient wetting of the restoration or structure being sprayed. Thus, for example, there is a good adherence between the glaze and porcelain restoration or ceramic surface.

With respect to the spraying and coating methods of the present invention, spray glaze of the present invention can be applied over the ceramic stains used in characterization of the dental restoration to more closely match a patient's natural dentition. This process allows the technician to apply the stains (usually over a restoration that has been coated with the opaque porcelain and translucent porcelain of the present invention), dry them under the muffle of the porcelain furnace then apply the glaze over the top of the stains to lock them under the glaze without distorting them during the firing cycle. This was not possible in the past because the stains would have to be fired to set them before the brushed on glaze could be applied as if the stains were not fired the glaze would blur or wash out the details and colors of the stains. In certain embodiments, the technique of the present invention allows the technician to only fire the restoration one time verses two firings using the old brush technique.

Fingerprint Formulation and Method

As stated above, embodiments of the present invention include a spray fingerprint composition that can be used in the process of lifting fingerprints on a surface and a method of obtaining fingerprints from a surface.

Fingerprints are used to identify an unknown victim, witness, or suspect, to verify records, and most importantly, as links and matches between a suspect and a crime. Occasionally, a print is found that is made with the palm of the hand or a bare foot. These are ordinarily processed by the same methods used for fingerprints. Accordingly, the term "fingerprint" used with respect to the present invention includes palm prints or foot prints.

Ridges develop on the skin of its fingers and thumbs. These ridges arrange themselves in more or less regular patterns. For purposes of classification, experts divide these ridge patterns into three basic classes: arches, loops, and whorls. When prints are found, an expert compares them with samples.

There are three basic forms of prints: plastic, which are impressions left in soft material like wax, paint, or putty; visible, which are made by blood, dirt, ink, or grease; and latent, which are normally invisible and must be developed before they can be seen and photographed.

The most common way of developing latent prints is by dusting with fingerprint powders. A very fine powder is gently brushed over the surface of an object suspected of having fingerprints. The fine powder sticks to the oils and perspiration that are left behind from the top of the friction ridges of the skin. Great care and skill are required to actualize the latent print. A non-skilled person may cause damage to the ridged line of the fingerprint during the brushing step.

Powders of varying color are used to get the maximum contrast with the background material. The excess powder is blown off, leaving a clear impression from the powder that adheres to the ridges of the print. The print can then be photographed and lifted with an adhesive material such as tape.

U.S. Pat. No. 6,299,674 to Takamuru et al., incorporated herein by reference, generally discusses fingerprinting methods and discloses a fingerprint detecting agent and method which can be used to detect latent fingerprints being in a wet condition.

U.S. Pat. No. 4,176,205 to Molina, incorporated herein by reference, generally discusses fingerprinting methods and discloses a fingerprint powder and a method for developing latent prints. The fingerprint powder of Molina can be applied by blowing the powder over a surface containing latent prints, or by brushing by pouring the powder on such surface to reveal a print that can be photographed or lifted by applying tape or a strippable coating over the print.

The fingerprint spray formulation of the present invention has at least two advantages in that it allows latent prints to be actualized with greater ease and with as little damage as possible to the print. Brushing has the potential to damage the print. Furthermore, the method of the present invention allows a greater area to be dusted in much less time than with dusting.

An aerosolized spray fingerprint dusting powder, comprising (weight %): about 5-70% fingerprinting powder; about 5-60% wetting agent; and about 10-70% non-CFC propellant.

The fingerprint powder of the present invention is not known to be critical. That is, any fingerprint powder known in the art is capable of being used with the present invention. For example, the fingerprinting powder may be selected from the group consisting of talc, silica, barium sulfate, calcium carbonate, gypsum, alumina, agalmatolite, lithopone, zinc oxide, silicon oxide, titanium oxide, carbon black, graphite, molybdenum disulfide, iron oxide, silica black, chrome black, mineral black, vine black, bone black, silicon carbonate, and mixtures thereof.

In examples of this embodiment, the particle sizes may be the same particle sizes described above for the opaque and glaze spray compositions. Additionally, the wetting agent and propellant may be the same as described above with respect to the glaze and opaque compositions.

The aerosolized spray fingerprint dusting powder compositions of the present invention may be used for obtaining fingerprints. This method comprises identifying a surface that may contain a latent fingerprint; spraying the surface with the fingerprint dusting powder to actualize latent print; and analyzing actualized print. Additionally, the actualized print may be documented by photographing the actualized print or removing the actualized print with an adhesive material.

EXAMPLES

The following examples are presented to further illustrate the invention. But, it should be recognized that the invention is not to be considered limited thereto.

Example 1

This Example is a preferred spray glaze composition. 22.5 grams of Ferro Corporation 3227 leadless glass frit is milled until about 90% or more of the particles have a particle size of less that 25 microns, and is added to 45 grams of 99% anhydrous isopropyl alcohol in an aluminum 202×214 lined aerosol spray can container manufactured by CCL Container Corporation, Hermitage, Pa. The container is supplied with an internal mixing ball. 100 grams of A-31 propellant is added to the contents of the aerosol spray container. All the materials are thoroughly mixed and the spray container crimped and sealed. More specifically, This provides the aerosolized spray glaze with a pressure of about 31 psig at 70 degrees Fahrenheit.

The aerosol spray container is equipped with a spray valve assembly available from Precision Valve Company, Inc., of New York, and is ready for spraying. In this example, the valve assembly comprises an actuator (Part No. 01-9169-00); stem (04-0518-42); stem gasket (05-0420-07); spring (06-6044-00); body (07-1202-00); dip tube (09-2010-51); misc (11-0913-00); and mounting cup (32-8990-15).

Example 2

This is an example of a preferred spray opaque composition. 20 grams of dental opaque furnished by C-Mix Corporation, of Delray Beach, Fla. is added to 18 grams of 99% anhydrous isopropyl alcohol in an aluminum 202×214 lined aerosol spray container manufactured by CCL Container Corporation, Hermitage, Pa. These materials are thoroughly mixed and the spray container crimped and sealed. The container is supplied with an internal mixing ball. The container is then charged with 132 grams of A-31 propellant. This provides the aerosolized spray glaze with a pressure of about 31 psig at 70 degrees Fahrenheit. The aerosol spray can container is equipped with a spray valve assembly available from Precision Valve, and is ready for spraying.

Example 3

This is an example of a preferred opaque application procedure. A metal dental restoration is provided by Lloyd Dental Laboratory Inc. of Brentwood, Tenn.

An aerosolized spray opaque canned composition is prepared as described in Example 2 above.

Each of the restorations are carefully cleaned of all dirt and oil. The opaque spray container is shaken vigorously for about a minute or less to bring the opaque into full suspension and to fully mix the contents of the composition. After shaking, the composition and the restoration are brought into position for application of the spray opaque material to the metal surface. Care is taken no to hold the aerosol container at a sufficient distance from the restoration. If held to closely, droplets of the opaque material may appear on the restoration. In this example, the nozzle of the container is about 6 to 14 inches from the restoration. Additionally, in this Example the restorations were held with hemostats in front of a suction device to take away over spray.

Once a coating of the opaque material appears over the entire outer surface of the metal substructure, the metal-substructure is then fired in accordance with the instructions from the opaque porcelain manufacturer. In this Example, a second coat of opaque material is applied and the metal-substructure is fired again. The metal-substructure is now ready for porcelain body build-up, ground-in to shape, and fired forming the dental restoration.

Example 4

This example demonstrates applying glaze to a porcelain restoration of Example 3. The porcelain restoration is carefully cleaned and placed on a ceramic pillow on top of a ceramic firing tray. Next the glaze container is shaken thoroughly for approximately a minute or less and the internal mixing ball moved freely to bring the glass frit into a suspended state and completely mix the entire contents. If the application is sprayed too close to the restoration an excessive amount of glaze accumulates to create an over glazed or to smooth look, while filling in esthetic details of the restoration. Some puddling of glaze occurred when a sufficient distance was not maintained or the glaze was not applied in short burst.

In this example, the spray glaze is applied from a distance of about 8 to 14 inches. The spray glaze is sprayed in short bursts from four (4) different directions around the side of the restorations on the tray and then sprayed from overhead for the final coating before firing. The container is shaken after each burst. A light dusting of glaze over the entire surfaces of the restorations is observed.

The restoration is fired to between 1300 and 1730 degrees Fahrenheit, depending on the type of porcelain used to manufacture the restoration and in accordance with the firing instructions of the glaze manufacturer. A glaze of excellent quality resulted.

Example 5

This example demonstrates incorporating a stain into a dental restoration of the present invention. A dental restoration is coated as described in Example 3. A marking is applied to the restoration that resembles a natural tooth stain. The restoration is then coated with a glaze as shown in Example 4.

Example 6

This example demonstrates how the spray glaze of the present invention can be used to glaze coat hobby craft items and pottery pieces. The object to glazed should be cleaned to remove any accumulated dust or dirt, the item is then placed in the appropriate spray area for spray glazing. The spray glaze container is shaken vigorously for about 1 minute so that the mixing ball moves freely to bring the glass frit into a suspended state and to completely mix the entire contents. Attention should be taken not to over glaze any part of the item, this condition can be controlled by continually moving the spray can in even paths around the item covering all flat and round surfaces evenly.

In this application, short controlled bursts provide more control than long spray sequences. After coating the entire object with sprayed glaze, inspection of the object should take place to see if any additional glaze should be applied to even out the coating. This inspection is made possible due to the alcohol carrier evaporating leaving only a visible layer of powder glaze. It may be desirable to spray a ceramic sealer spray on the item if one is to move the glazed item some distance.

The item at this time is ready for firing at the manufacturers suggested Cone temperature which usually ranges between Cone 4 and Cone 7.

Example 7

This example demonstrates how the spray glaze of the present invention can be used to coat ceramic tile for indoor or outdoor uses. The tile/s should be cleaned of any accumulated dust or dirt, the tile/s should then be placed in the appropriate spray area for spray glazing. The spray glaze container is shaken vigorously for about 1 minute so that the mixing ball moves freely to bring the glass frit into a suspended state and to completely mix the entire contents. Once the tile/s are situated, a coating of spray glaze can be applied to the entire tile area with short controlled bursts of spray glaze, careful attention should be taken not to over glaze any part of the item. The tile/s can be prepared with pre-designed templates of any chosen material or design to cover or expose any desirable portion of tile/s before glazing. This application method will allow for multiple colors to be applied in any chosen design or color combination.

In this application, short evenly directed bursts of spray glaze should be applied in even paths allowing the alcohol carrier to evaporate leaving only a dry powder glaze layer for visual inspection. After this visual inspection, a second coating may be necessary to thoroughly coat the tile/s as desired to achieve the desired luster and/or finish. It may be desirable to spray a ceramic sealer spray on the tile or tiles if they are to be transported some distance after spray glazing.

Ceramic tiles with spray glaze coatings should be fired to the recommended temperature of the manufacturer. Firing temperatures vary depending on the type of tile and its intended use.

In summary, numerous benefits will result from employing the concepts of the present invention composition. The compositions and methods described herein are very expedient in its application requiring minimal experience or skill by an untrained individual with the procedure to apply an even uniform layer of glaze or opaque to a restoration. It also is effectively applied over stains without a complete full firing. Therefore, the production time required to complete dental restorations is significantly reduced.

The invention thus being described, it would be obvious that the same may be varied in many ways. Such variations should not be regarded as a departure from the spirit and scope of the present invention, and all such variations as would be obvious to one of ordinary skill in the art are intended to be included within the scope of the following claims.

This application references various patents and/or publications. All such patents and/or publications are expressly incorporated herein by reference in their entirely.

Finally, unless otherwise indicated, all numbers expressing quantities of ingredients, reaction conditions, and so forth as used in the specification and claims are to be understood as being modified by the term "about." Accordingly, unless specifically indicated to the contrary, the numerical parameters set forth in this specification and claims are approximations that may vary depending on the desired properties sought to be obtained by the present invention.

Notwithstanding that the numerical ranges and parameters setting forth the broad scope of the inventions are approximations, numerical values set forth in the specific examples are reported as precisely as possible.

We claim:

1. A pressurized spray delivery system, comprising:
   a sealed container housing a pressurized composition at a pressure of between 17 to 132 psig and a mixing ball; and
   an aerosol spray valve assembly with an actuator that releases the composition from the container when engaged;
   wherein the composition comprises (by weight %):
      about 10 to about 30% glass frit, with at least 90% of the glass frit particles having a particle size of about 25 microns or less;
      about 10 to about 40% wetting agent that includes alcohol; and
      about 40 to about 70% non-CFC propellant; and
   wherein the composition does not comprise trichlorotrifluoroethane.

2. The pressurized spray delivery system of claim 1, wherein the composition further includes an opaque material.

3. The pressurized spray delivery system of claim 1, wherein the glass frit is wet-milled.

4. The pressurized spray delivery system of claim 2, wherein the opaque material comprises about 10 to about 30% of the composition.

5. The pressurized spray delivery system of claim 2, wherein the opaque material contains glass frit particles, with about 90% of the glass frit particles having a particle size of about 25 microns or less.

6. The pressurized spray delivery system of claim 1, wherein the alcohol in the wetting agent is selected from methyl alcohol, ethyl alcohol, isopropyl alcohol, or mixtures thereof.

7. The pressurized spray delivery system of claim 1, wherein the non-CFC propellant is a hydrocarbon propellant.

8. The pressurized spray delivery system of claim 7, wherein the hydrocarbon propellant is selected from the group consisting of isobutane, butane, and mixtures thereof.

9. The pressurized spray delivery system of claim 1, wherein the composition consists essentially of (by weight %):
   about 14 to about 22% glass frit that has been wet milled, with at least 90% of the glass frit particles having a particle size of about 25 microns or less;
   about 28 to about 36% wetting agent that includes alcohol; and
   about 44 to about 56% non-CFC propellant.

10. The pressurized spray delivery system of claim 1, wherein the composition consists essentially of (by weight %):

about 21 to about 28% of an opaque material that includes glass frit that has been wet milled, with at least 90% of the glass frit particles having a particle size of about 25 microns or less;

about 15 to about 22% wetting agent that includes alcohol; and about 50 to about 62% non-CFC propellant.

* * * * *